(12) United States Patent
Irvin et al.

(10) Patent No.: US 9,042,712 B2
(45) Date of Patent: May 26, 2015

(54) HEATED AIR FRESHENER FOR 12V RECEPTACLE

(71) Applicant: American Covers, Inc., Draper, UT (US)

(72) Inventors: Aaron Irvin, Salt Lake City, UT (US); Nate Finlay, Lehi, UT (US)

(73) Assignee: American Covers, Inc., Draper, UT (US)

( * ) Notice: Subject to any disclaimer, the term of this patent is extended or adjusted under 35 U.S.C. 154(b) by 290 days.

(21) Appl. No.: 13/798,793

(22) Filed: Mar. 13, 2013

(65) Prior Publication Data

US 2014/0112649 A1    Apr. 24, 2014

Related U.S. Application Data

(60) Provisional application No. 61/717,515, filed on Oct. 23, 2012.

(51) Int. Cl.
*A61M 16/00* (2006.01)
*A61H 33/12* (2006.01)
*A61L 9/03* (2006.01)

(52) U.S. Cl.
CPC . *A61L 9/03* (2013.01); *A61L 9/032* (2013.01); *A61L 2209/12* (2013.01)

(58) Field of Classification Search
None
See application file for complete search history.

(56) References Cited

U.S. PATENT DOCUMENTS

| | | |
|---|---|---|
| D176,671 S | 4/1876 | Myers |
| 369,878 A | 9/1887 | Palmer |
| 1,171,737 A | 2/1916 | Madgan |
| 2,244,944 A | 6/1941 | Furlonge |
| D140,109 S | 1/1945 | Pierce |
| 2,733,333 A | 1/1956 | Peters |
| D177,826 S | 5/1956 | Katz |
| D178,237 S | 7/1956 | Katz |
| 3,239,145 A | 3/1966 | Aurelio |
| 3,456,106 A | 7/1969 | Glchkin |
| 3,655,129 A | 4/1972 | Seiner |
| 3,847,305 A | 11/1974 | Tobin |

(Continued)

FOREIGN PATENT DOCUMENTS

| | | |
|---|---|---|
| CA | 2077251 | 5/1993 |
| EP | 0 348 970 | 1/1990 |

(Continued)

OTHER PUBLICATIONS

U.S. Appl. No. 13/282,035; filed Oct. 26, 2011; Nathaniel Finlay; office action dated Jul. 17, 2013.

(Continued)

*Primary Examiner* — Thor Campbell

(57) ABSTRACT

An air freshener is configured to be carried by a power outlet of an automobile. The air freshener includes a scent capsule disposed in a housing. A heat source is disposed in the housing adjacent and opposing a permeable membrane of the scent capsule. The heat source is configured to heat the fragrant material in the scent capsule and accelerate permeation of the fragrant material through the permeable membrane of the sent capsule. A hatch is pivotally coupled to the housing and substantially contained within a hatch cavity with an outer surface that is substantially flush with an exterior of the housing in a closed position. The hatch can include a capsule cavity therein, carrying the scent capsule, and facing an interior of the housing in the closed position.

25 Claims, 11 Drawing Sheets

(56) References Cited

U.S. PATENT DOCUMENTS

| | | | |
|---|---|---|---|
| 3,948,445 A | 4/1976 | Andeweg | |
| 3,971,858 A | 7/1976 | Collier et al. | |
| D246,986 S | 1/1978 | Costello | |
| 4,084,079 A | 4/1978 | Costello | |
| D250,041 S | 10/1978 | Schimanski | |
| 4,149,675 A | 4/1979 | Van Breen et al. | |
| 4,184,099 A | 1/1980 | Lindauer et al. | |
| 4,214,146 A * | 7/1980 | Schimanski | 392/390 |
| 4,226,944 A | 10/1980 | Stone et al. | |
| D258,511 S | 3/1981 | Ashton | |
| 4,280,649 A | 7/1981 | Montealegre | |
| 4,301,949 A | 11/1981 | Palson et al. | |
| 1,683,545 A | 9/1982 | Harris | |
| 4,382,548 A | 5/1983 | van der Heijden | |
| 4,391,781 A | 7/1983 | van Lit | |
| 4,517,326 A | 5/1985 | Cordts et al. | |
| 4,549,693 A | 10/1985 | Barlics | |
| 4,594,380 A | 6/1986 | Chapin et al. | |
| D286,323 S | 10/1986 | Haworth | |
| 4,638,057 A | 1/1987 | Takahashi et al. | |
| 4,649,046 A | 3/1987 | Kross | |
| 4,703,070 A | 10/1987 | Locko et al. | |
| RE32,834 E | 1/1989 | Cordts et al. | |
| 4,808,347 A | 2/1989 | Dawn | |
| 4,840,773 A | 6/1989 | Wade | |
| 4,849,606 A | 7/1989 | Martens et al. | |
| 4,874,129 A | 10/1989 | DiSapio et al. | |
| 4,880,690 A | 11/1989 | Szycher et al. | |
| 4,950,542 A | 8/1990 | Barker | |
| 4,967,988 A | 11/1990 | Nguyen | |
| 4,968,456 A | 11/1990 | Muderlak et al. | |
| 5,008,115 A | 4/1991 | Lee et al. | |
| 5,019,434 A | 5/1991 | Matsumoto | |
| 5,034,222 A | 7/1991 | Kellett et al. | |
| D319,781 S | 9/1991 | Halm et al. | |
| 5,050,798 A | 9/1991 | Sulivan | |
| D322,558 S | 12/1991 | Halm et al. | |
| 5,071,704 A | 12/1991 | Fischel-Ghodsian | |
| 5,114,625 A | 5/1992 | Gibson | |
| 5,120,583 A | 6/1992 | Garcia | |
| 5,178,327 A | 1/1993 | Palamand et al. | |
| 5,180,107 A | 1/1993 | Lindauer | |
| 5,193,445 A | 3/1993 | Fergon | |
| D334,975 S | 4/1993 | Bunce | |
| 5,208,027 A | 5/1993 | Weder et al. | |
| 5,220,636 A | 6/1993 | Chang | |
| D338,519 S | 8/1993 | Peterson | |
| 5,234,162 A | 8/1993 | Sullivan | |
| 5,240,487 A | 8/1993 | Kung | |
| D340,358 S | 10/1993 | Liu | |
| D349,157 S | 7/1994 | Rymer | |
| D350,192 S | 8/1994 | Patel et al. | |
| 5,368,822 A | 11/1994 | McNeil | |
| 5,373,581 A * | 12/1994 | Smith | 392/390 |
| 5,394,506 A * | 2/1995 | Stein et al. | 392/395 |
| 5,407,642 A | 4/1995 | Lord | |
| 5,422,078 A | 6/1995 | Colon | |
| D367,526 S | 2/1996 | Bignon | |
| D367,924 S | 3/1996 | Patel et al. | |
| 5,520,921 A | 5/1996 | Chalifoux | |
| D373,626 S | 9/1996 | Dente et al. | |
| D375,350 S | 11/1996 | Patel et al. | |
| 5,595,194 A | 1/1997 | Talbot | |
| D380,258 S | 6/1997 | Muller et al. | |
| 5,651,522 A | 7/1997 | Davis et al. | |
| 5,683,285 A | 11/1997 | Wong | |
| 5,695,692 A | 12/1997 | Kennedy | |
| 5,704,832 A | 1/1998 | Borrell | |
| D390,941 S | 2/1998 | Cessaroni et al. | |
| D392,032 S | 3/1998 | Zaragoza et al. | |
| 5,762,549 A | 6/1998 | Scheuer et al. | |
| 5,780,527 A | 7/1998 | O'Leary | |
| 5,820,791 A | 10/1998 | Canale | |
| D400,662 S | 11/1998 | Davis | |
| 5,845,847 A | 12/1998 | Martin et al. | |
| 5,860,552 A | 1/1999 | Culhane et al. | |
| 5,861,128 A | 1/1999 | Vick et al. | |
| D404,957 S | 2/1999 | Cheris et al. | |
| 5,871,765 A | 2/1999 | Johnson et al. | |
| 5,899,382 A | 5/1999 | Hayes | |
| D410,540 S | 6/1999 | Pinchuk | |
| D411,002 S | 6/1999 | Farmer | |
| D415,267 S | 10/1999 | Kauzlarich et al. | |
| D415,268 S | 10/1999 | Farmer | |
| 5,988,520 A | 11/1999 | Bitner | |
| D417,727 S | 12/1999 | Christianson | |
| 6,044,202 A | 3/2000 | Junkel | |
| D424,677 S | 5/2000 | Chen | |
| D425,190 S | 5/2000 | Morikawa | |
| 6,102,660 A | 8/2000 | Lee | |
| 6,104,866 A * | 8/2000 | DeWitt et al. | 392/390 |
| 6,111,055 A | 8/2000 | Berger et al. | |
| 6,123,906 A | 9/2000 | Farmer | |
| 6,123,935 A | 9/2000 | Wefler et al. | |
| D432,222 S | 10/2000 | Rymer et al. | |
| D435,694 S | 12/2000 | Lebherz | |
| D437,038 S | 1/2001 | Chuan | |
| D437,041 S | 1/2001 | Eisenbraun | |
| 6,190,607 B1 | 2/2001 | Farmer | |
| 6,191,197 B1 | 2/2001 | Wang et al. | |
| 6,197,263 B1 | 3/2001 | Blount | |
| 6,202,938 B1 | 3/2001 | Collier | |
| D440,294 S | 4/2001 | Bilek | |
| D441,441 S | 5/2001 | Upson | |
| 6,264,887 B1 | 7/2001 | Farmer | |
| 6,291,371 B1 | 9/2001 | Shefer et al. | |
| 6,309,715 B1 | 10/2001 | Lindauer et al. | |
| 6,325,475 B1 | 12/2001 | Hayes et al. | |
| D454,190 S | 3/2002 | Trocola | |
| 6,357,260 B1 | 3/2002 | Lutz | |
| 6,374,044 B1 | 4/2002 | Freide | |
| 6,375,966 B1 | 4/2002 | Maleeny et al. | |
| 6,379,689 B1 | 4/2002 | Aguadisch | |
| 6,416,043 B1 | 7/2002 | Eisenbraun | |
| 6,514,467 B1 | 2/2003 | Bulsink et al. | |
| D472,968 S | 4/2003 | Christianson | |
| D478,379 S | 8/2003 | Talenton et al. | |
| D478,973 S | 8/2003 | Wagner | |
| 6,609,935 B2 * | 8/2003 | Huang | 439/620.16 |
| D479,592 S | 9/2003 | Lammel et al. | |
| D485,343 S | 1/2004 | Wu | |
| D487,504 S | 3/2004 | Yuen | |
| 6,712,286 B2 | 3/2004 | Baxter et al. | |
| D488,214 S | 4/2004 | Quantin | |
| D488,548 S | 4/2004 | Lablaine | |
| D491,257 S | 6/2004 | Picken | |
| D491,798 S | 6/2004 | Buthier | |
| D496,720 S | 9/2004 | Dudley | |
| 6,800,252 B1 | 10/2004 | Jedzinski | |
| 6,885,811 B2 | 4/2005 | He et al. | |
| D504,943 S | 5/2005 | Dudley | |
| D507,341 S | 7/2005 | Taylor | |
| D511,568 S | 11/2005 | Wheatley | |
| D514,679 S | 2/2006 | Wheatley | |
| D515,192 S | 2/2006 | Smith et al. | |
| 7,025,283 B2 | 4/2006 | Torres | |
| 7,055,764 B1 | 6/2006 | Martinez et al. | |
| 7,061,386 B2 | 6/2006 | Seresini | |
| 7,070,172 B2 | 7/2006 | Fabrega et al. | |
| 7,137,570 B2 | 11/2006 | Wheatley et al. | |
| 7,141,215 B2 * | 11/2006 | Guan et al. | 422/125 |
| D535,376 S | 1/2007 | Michaels et al. | |
| D535,379 S | 1/2007 | Hundertmark | |
| 7,159,792 B2 | 1/2007 | Wheatley et al. | |
| D544,080 S | 6/2007 | Carlson | |
| D544,084 S | 6/2007 | Michaels et al. | |
| D544,594 S | 6/2007 | Zobele | |
| D544,953 S | 6/2007 | Kee | |
| D546,432 S | 7/2007 | Hundertmark | |
| 7,243,859 B2 | 7/2007 | Caserta et al. | |
| D548,317 S | 8/2007 | Newton et al. | |
| D550,345 S | 9/2007 | Weggelaar | |
| D551,333 S | 9/2007 | Wu | |
| 7,285,248 B2 | 10/2007 | Yamamoto et al. | |

(56) References Cited

U.S. PATENT DOCUMENTS

| | | | |
|---|---|---|---|
| D554,746 S | 11/2007 | Davis et al. | |
| 7,293,719 B2 | 11/2007 | Wheatley | |
| D565,162 S | 3/2008 | Carlson | |
| 7,344,123 B2 | 3/2008 | Pankhurst et al. | |
| D565,715 S | 4/2008 | Wu | |
| D573,706 S | 7/2008 | Zlotnik et al. | |
| D574,941 S | 8/2008 | Weggelaar | |
| 7,441,360 B2 | 10/2008 | Christianson et al. | |
| D580,039 S | 11/2008 | Zlotnik et al. | |
| D585,129 S | 1/2009 | Huang | |
| D585,971 S | 2/2009 | Carrizales | |
| D591,415 S | 4/2009 | Wu | |
| D593,670 S | 6/2009 | Valentiono et al. | |
| D594,953 S | 6/2009 | King et al. | |
| D594,954 S | 6/2009 | Wheatley | |
| 7,544,331 B1 * | 6/2009 | Pettaway | 422/125 |
| 7,544,332 B2 | 6/2009 | De Silva et al. | |
| D597,645 S | 8/2009 | Thompson | |
| D598,531 S | 8/2009 | Irvin | |
| D604,825 S | 11/2009 | Brandenburg | |
| D607,983 S | 1/2010 | Irvin | |
| 7,651,666 B2 | 1/2010 | Adair et al. | |
| 7,670,566 B2 | 3/2010 | Adair et al. | |
| 7,687,037 B2 | 3/2010 | Wheatley | |
| 7,687,038 B2 | 3/2010 | Wheatley | |
| D614,277 S | 4/2010 | Hsiao | |
| D619,692 S | 7/2010 | Hami et al. | |
| D619,693 S | 7/2010 | Hami et al. | |
| D619,694 S | 7/2010 | Hami et al. | |
| D620,573 S | 7/2010 | Hami et al. | |
| D622,835 S | 8/2010 | Mendheim | |
| 7,780,094 B2 | 8/2010 | Caserta et al. | |
| D625,798 S | 10/2010 | Hami et al. | |
| D629,881 S | 12/2010 | Valentino et al. | |
| D631,534 S | 1/2011 | Kajizuka | |
| D631,954 S | 2/2011 | Bertassi et al. | |
| D633,610 S | 3/2011 | Wu | |
| D637,275 S | 5/2011 | Baraky | |
| D640,358 S | 6/2011 | Irvin | |
| D640,781 S | 6/2011 | Brandenburg | |
| D642,668 S | 8/2011 | Lablaine | |
| D645,949 S | 9/2011 | Brandenburg et al. | |
| D647,186 S | 10/2011 | Chan et al. | |
| D649,237 S | 11/2011 | Bilko et al. | |
| D650,892 S | 12/2011 | Wheatley | |
| 8,090,244 B2 * | 1/2012 | Belongia et al. | 392/403 |
| 8,147,761 B2 | 4/2012 | Wheatley et al. | |
| D660,950 S | 5/2012 | Finlay | |
| D662,581 S | 6/2012 | Savegnago | |
| 8,197,761 B1 | 6/2012 | Miller-Larry | |
| 8,251,299 B1 | 8/2012 | Irvin | |
| D667,100 S | 9/2012 | Hakim | |
| 8,485,454 B1 | 7/2013 | Irvin | |
| 8,490,846 B1 | 7/2013 | Wheatley | |
| 2003/0097936 A1 | 5/2003 | Maleeny et al. | |
| 2003/0199421 A1 | 10/2003 | Copfer | |
| 2004/0265164 A1 | 12/2004 | Woo et al. | |
| 2005/0127538 A1 | 6/2005 | Fabrega et al. | |
| 2005/0169793 A1 | 8/2005 | Wheatley et al. | |
| 2006/0043216 A1 | 3/2006 | Robinson | |
| 2006/0078477 A1 | 4/2006 | Althoe et al. | |
| 2006/0196964 A1 | 9/2006 | Wheatley et al. | |
| 2006/0279008 A1 | 12/2006 | Jursich | |
| 2007/0057084 A1 | 3/2007 | Vieira | |
| 2007/0160492 A1 | 7/2007 | Spector | |
| 2007/0290064 A1 | 12/2007 | Majerowski et al. | |
| 2008/0099576 A1 | 5/2008 | Hart | |
| 2008/0128925 A1 | 6/2008 | Pankhurst et al. | |
| 2009/0004420 A1 | 1/2009 | Wheatley | |
| 2009/0008411 A1 | 1/2009 | Schumacher et al. | |
| 2009/0010813 A1 | 1/2009 | Wang et al. | |
| 2009/0072045 A1 | 3/2009 | Wheatley et al. | |
| 2009/0148142 A1 * | 6/2009 | McGee et al. | 392/387 |
| 2009/0173799 A1 | 7/2009 | Litten-Brown et al. | |
| 2009/0196587 A1 * | 8/2009 | Cheung | 392/394 |
| 2010/0010409 A1 | 1/2010 | Irvin | |
| 2010/0019059 A1 | 1/2010 | Bulsink et al. | |
| 2010/0065654 A1 | 3/2010 | Wheatley et al. | |
| 2010/0187327 A1 | 7/2010 | Irvin | |
| 2010/0288847 A1 | 11/2010 | Gruenbacher et al. | |
| 2011/0108632 A1 | 5/2011 | Brandenburg et al. | |
| 2011/0110823 A1 | 5/2011 | Wheatley | |
| 2012/0076276 A1 | 3/2012 | Wang et al. | |
| 2013/0028798 A1 | 1/2013 | Irvin | |

FOREIGN PATENT DOCUMENTS

| | | |
|---|---|---|
| EP | 1 346 734 | 9/2003 |
| WO | WO 00/24434 | 5/2000 |
| WO | WO 00/64498 | 11/2000 |
| WO | WO 02/35975 | 5/2002 |
| WO | WO 02/38029 | 5/2002 |
| WO | WO 2006/010282 | 2/2006 |
| WO | WO 2006/084160 | 8/2006 |
| WO | WO 2004/078219 | 1/2007 |
| ZA | 20004637 | 9/2000 |

OTHER PUBLICATIONS

U.S. Appl. No. 12/979,795; filed Dec. 28, 2010; Aaron Irvin; office action dated Oct. 18, 2013.

U.S. Appl. No. 13/940,074; filed Jul. 11, 2013; Alan J. Wheatley; office action dated Nov. 20, 2013.

U.S. Appl. No. 12/915,924; filed Oct. 29, 2010; Nathaniel Finlay; notice of allowance dated Nov. 22, 2013.

U.S. Appl. No. 13/282,035; filed Oct. 26, 2011; Nathaniel Finlay; notice of allowance dated Nov. 26, 2013.

U.S. Appl. No. 13/281,890; filed Oct. 26, 2011; Aaron Irvin; notice of allowance dated Dec. 10, 2013.

About.com Housekeeping, http://housekeeping.about.com/od/pr . . . affresh, Febrezee Noticeables, accessed Oct. 2, 2008, 2 pages.

Aromate E-News, Innovation in Novelty Fragrance, Http://209.85.173.104/seasrch?qcach . . . , accessed Oct. 8, 2008, 2 pages.

ecrater, www.ecrater.com/product.hp? . . . , Yankee Candle Selects Two Scents Electric Fragrance Unit Macintosh/Home Sweet Home, accessed Oct. 2, 2008, 1 page.

http://decomodo.com/articles/categor/lighting/, Bamboo Pillar Candle, Jan. 8, 2008, 1 page.

http://shop.advanceautoparts.com/webapp/wcs/stores/servlet/product_6170795-P_N3004 . . . Advance Auto Part; Arometrics Dual-Scent Vent-Juicy Strawberry and Vanilla; 1 Page; accessed Dec. 10, 2010.

http://www.bestliquidations.com/Medo_Vent Frehser.htm; BestLiquidations.com; Medo Vent Fresh Air Fresheners; 2 pages; accessed Dec. 10, 2010.

Medo® Air Fresheners; Auto Expressions™ 2005 Product Catalog; 25 pages.

Pictures (3) of Medo® auto Expressions Vent™ Air Freshener distributed by SOPUS Products of Moorpark , CA 2003 copyright date on package.

Scents & Sprays, www.scentsandsprays.com/ya . . . , Yankee Autumn Bounty Electric 2 Home Air Fresheners, copyright 2001-2008 scentsandsprays.com, accessed Oct. 2, 2008, 1 page.

www.4imprint.com/EXEC/DETAIL/FROMPRODUCT-GROUP/~SKU100300/~CA100300.htm, Hot Rod Vent Stick Air Freshener (it . . . , accessed Aug. 12, 2008, 2 pages.

www.autothing.com/Products/Air%20Fresheners/air%20freshener-clip.htm, Air Fresheners, Fresh Scents for you mobile Life, Clip-on Air Vent Clips rom Eagle o., Accessed Aug. 12, 2008, 1 page.

www.chicscents.com/Products.aspx Island Adventure Sandals; 2 pages; accessed Feb. 1, 2011.

www.chicscents.com/Products.aspx; Inspiration 3-D by Chic; 2 pages; accessed Feb. 1, 2011.

U.S. Appl. No. 12/979,763; filed Dec. 28, 2010; Aaron Irvin.

U.S. Appl. No. 12/979,795; filed Dec. 28, 2010; Aaron Irvin.

U.S. Appl. No. 12/979,813; filed Dec. 28, 2010; Aaron Irvin.

U.S. Appl. No. 13/191,966; filed Jul. 27, 2011; Aaron Irvin.

(56) References Cited

OTHER PUBLICATIONS

U.S. Appl. No. 12/915,983; filed Oct. 29, 2010; Alan J. Wheatley; notice of allowance dated Feb. 20, 2013.
U.S. Appl. No. 12/979,763; filed Dec. 28, 2010; Aaron Irvin notice of allowance dated Apr. 15, 2013.
U.S. Appl. No. 13/282,035; filed Oct. 26, 2011; Nathaniel Finlay, office action dated Apr. 17, 2013.
U.S. Appl. No. 12/987,662; filed Jan. 10, 2011; Alan J. Wheatley; notice of allowance dated Jun. 7, 2013.
U.S. Appl. No. 12/979,690; filed Dec. 28, 2010; Alan J. Wheatley; notice of allowance dated Jun. 10, 2013.
U.S. Appl. No. 12/979,601; filed Dec. 28, 2010; Alan J. Wheatley; notice of allowance dated Jun. 10, 2013.
U.S. Appl. No. 29/435,391; filed Oct. 23, 2012; Aaron Irvin, notice of allowance dated Jun. 18, 2013.

* cited by examiner

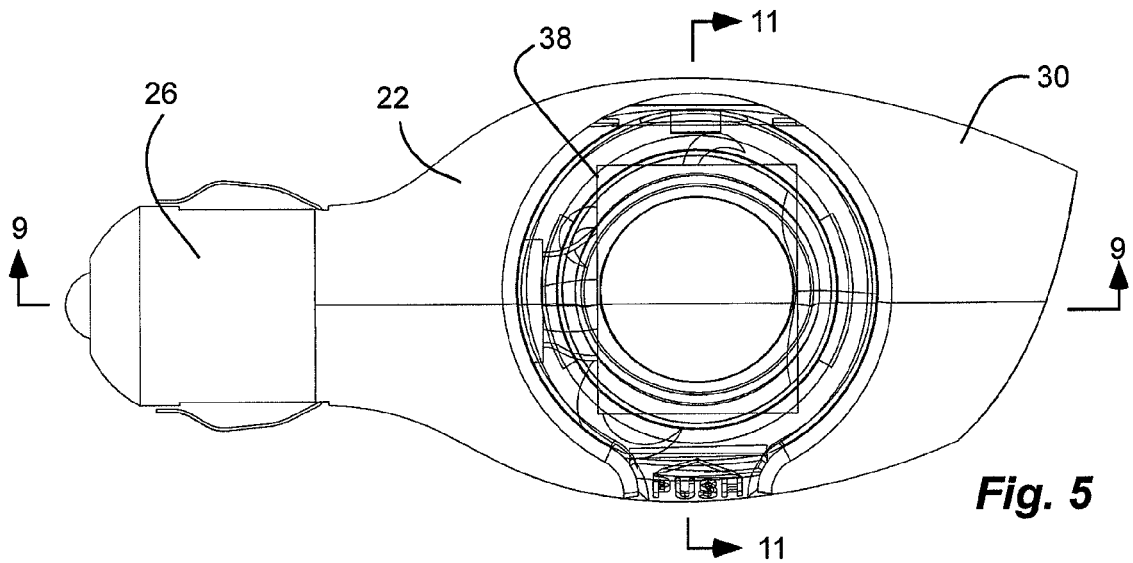
*Fig. 5*
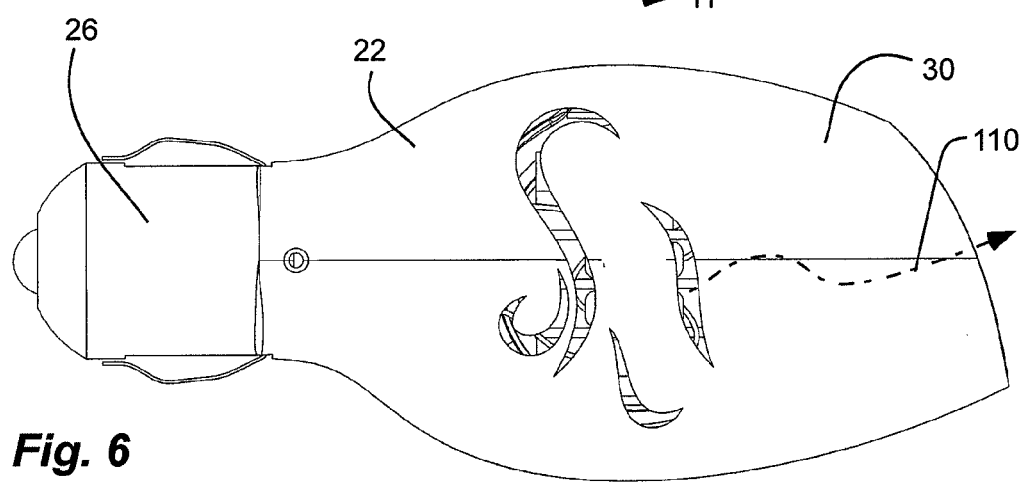
*Fig. 6*
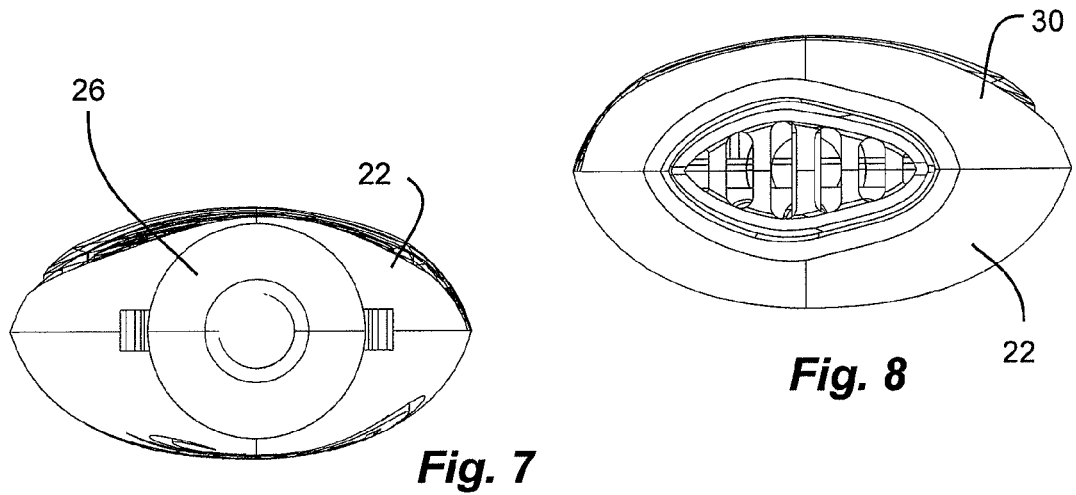
*Fig. 7*
*Fig. 8*

HEATED AIR FRESHENER FOR 12V RECEPTACLE

PRIORITY CLAIM

Priority is claimed to U.S. Provisional Patent Application Ser. No. 61/717,515, filed Oct. 23, 2012, which is hereby incorporated herein by reference.

RELATED APPLICATION(S)

This application is related to U.S. patent application Ser. No. 13/281,890, filed Oct. 26, 2011, which claims priority to U.S. Provisional Application Ser. No. 61/408,220, filed Oct. 29, 2010; which are hereby incorporated herein by reference.

This application is related to U.S. patent application Ser. No. 13/282,035, filed Oct. 26, 2011, which claims priority to U.S. Provisional Application Ser. No. 61/408,263, filed Oct. 29, 2010; which are hereby incorporated herein by reference.

BACKGROUND

1. Field of the Invention

The present invention relates generally to air fresheners.

2. Related Art

Automobile fan driven air fresheners have been proposed. See, for example, U.S. Pat. Nos. 4,968,456 and 4,808,347. Other air fresheners include a light source. See, for example, U.S. Pat. Nos. 7,293,719 and 7,687,037.

The improvement and development of air fresheners is an ongoing endeavor.

SUMMARY OF THE INVENTION

It has been recognized that it would be advantageous to develop an air freshener to provide a desired scent or neutralizing agent for use with a power outlet of an automobile. In addition, it has been recognized that it would be advantageous to develop an air freshener capable of accelerating the dispersal of scent. In addition, it has been recognized that it would be advantageous to develop an air freshener with replaceable or renewable scent.

The invention provides an air freshener to be carried by a power outlet of an automobile. The air freshener includes a housing with a stem and a head with a cavity therein. The stem is sized and shaped to be inserted into the power outlet of the automobile. A scent capsule is disposed in the housing and has a chamber containing a fragrant material and has a permeable membrane through which a fragrance of the fragrant material can permeate over time. A heat source is disposed in the housing adjacent and opposing the permeable membrane of the scent capsule, and capable of being powered by the power outlet of the automobile to heat the fragrant material in the scent capsule and accelerate permeation of the fragrant material through the permeable membrane of the sent capsule.

In accordance with a more detailed aspect of the present invention, the housing can include a hatch cavity in the head of the housing. A hatch can be pivotally coupled to the housing and substantially contained within the hatch cavity with an outer surface that is substantially flush with an exterior of the housing in a closed position, and with a capsule cavity therein facing an interior of the housing in the closed position. The scent capsule can be removably disposed in the capsule cavity of the hatch and carried by the hatch as the hatch pivots, with the permeable membrane facing the interior of the cavity in the closed position.

In addition, the invention provides an air freshener to be carried by a power outlet of an automobile. The air freshener includes a housing with a stem and a head with a cavity therein. The stem is sized and shaped to be inserted into the power outlet of the automobile. A hatch cavity is disposed in the head of the housing. A hatch is pivotally coupled to the housing and substantially contained within the hatch cavity with an outer surface that is substantially flush with an exterior of the housing in a closed position, and with a capsule cavity therein facing an interior of the housing in the closed position. A scent capsule is removably disposed in the capsule cavity of the hatch and carried by the hatch as the hatch pivots. The scent capsule has a chamber containing a fragrant material and has a permeable membrane through which a fragrance of the fragrant material can permeate over time. The permeable membrane faces the interior of the cavity in the closed position.

In accordance with a more detailed aspect of the present invention, a heat source can be disposed in the housing adjacent and opposing the permeable membrane of the scent capsule, and capable of being powered by the power outlet of the automobile to heat the fragrant material in the scent capsule and accelerate permeation of the fragrant material through the permeable membrane of the sent capsule.

Furthermore, the invention provides an air freshener to be carried by a power outlet of an automobile. The air freshener includes a housing with a stem and a head with a cavity therein. The stem is sized and shaped to be inserted into the power outlet of the automobile. A hatch cavity is disposed in the head of the housing. A hatch is pivotally coupled to the housing and substantially contained within the hatch cavity with an outer surface that is substantially flush with an exterior of the housing in a closed position, and with a capsule cavity therein facing an interior of the housing in the closed position. An exterior window is disposed in the outer surface of the hatch. An interior window is disposed in the hatch facing an interior of the cavity in the closed position. A scent capsule is removably disposed in the capsule cavity of the hatch and carried by the hatch as the hatch pivots. The scent capsule has a chamber containing a fragrant material and has a permeable membrane through which a fragrance of the fragrant material can permeate over time. The permeable membrane faces the interior of the cavity in the closed position. The chamber is at least light translucent. A heat plate is disposed in the housing adjacent the hatch cavity and opposes the permeable membrane of the scent capsule when the hatch is in the closed position configured to heat the fragrant material in the scent capsule and accelerate permeation of the fragrant material through the permeable membrane of the sent capsule. A light is disposed in the housing adjacent the interior window of the hatch when the hatch is in the closed position configured to illuminate the scent material in the scent capsule so that the scent material is visible through the exterior window of the hatch. An inlet vent is in the housing adjacent the heat plate. An outlet vent in the housing configured to allow release of the fragrant material from the housing. An air flow path is defined between the inlet vent and the outlet vent.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein:

FIG. 5 is a top view of the air freshener of FIG. 1;

FIG. 6 is a bottom view of the air freshener of FIG. 1;

FIG. 7 is an end view of the air freshener of FIG. 1;

FIG. 8 is an opposite end view of the air freshener of FIG. 1;

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENT(S)

Definitions

The term "power outlet" or "power outlet of an automobile or vehicle" is used herein to refer to any type of power outlet available in an automobile or vehicle, and which is typically a 12 volt outlet configured in the style to receive a cigarette lighter or other accessory. Such a power outlet can be located in a dash or console of a vehicle. Such a power outlet may also include an adapter inserted into the power outlet. Such a power outlet can be oriented horizontally, vertically, or at an incline.

The terms "top" and "bottom" and "downwardly" and "upwardly" and the like are used herein relative to the air freshener device or housing thereof being oriented upright or vertical; while it is understood that the device or housing can be oriented horizontally or at an incline during use depending on the orientation of the power outlet.

The term "scent material" and "fragrant material" are used interchangeably herein to refer broadly to a material that carries a desired fragrance or scent, or even a neutralizing agent.

The term "clear dome" is used herein to refer to a dome that is clear or transparent, or that is at least translucent.

Description

Figure 1:
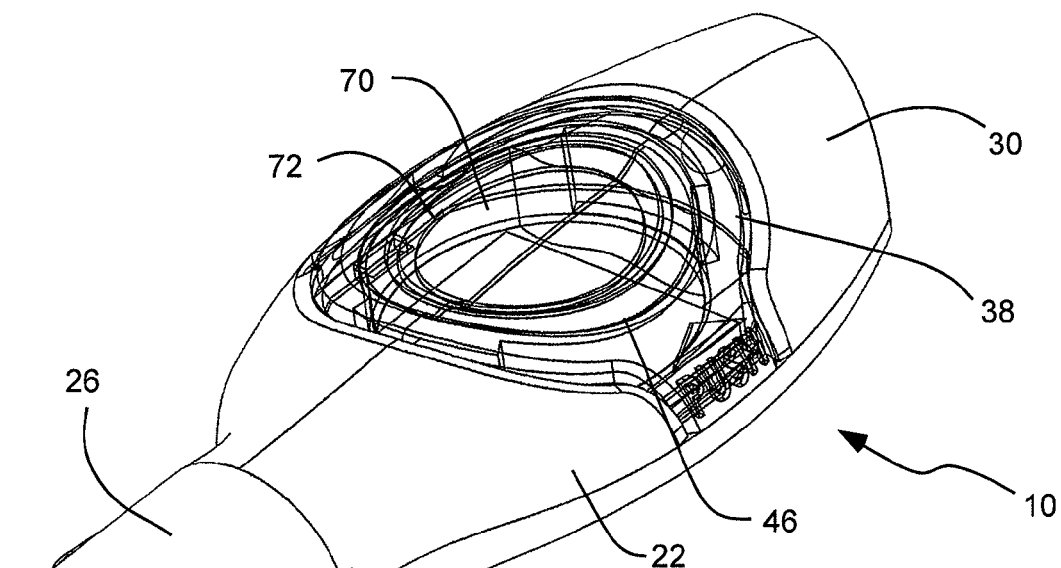
FIG. 1 is a perspective view of an air freshener in accordance with one embodiment of the present invention in which a catch is shown in a closed position.
Figure 2:
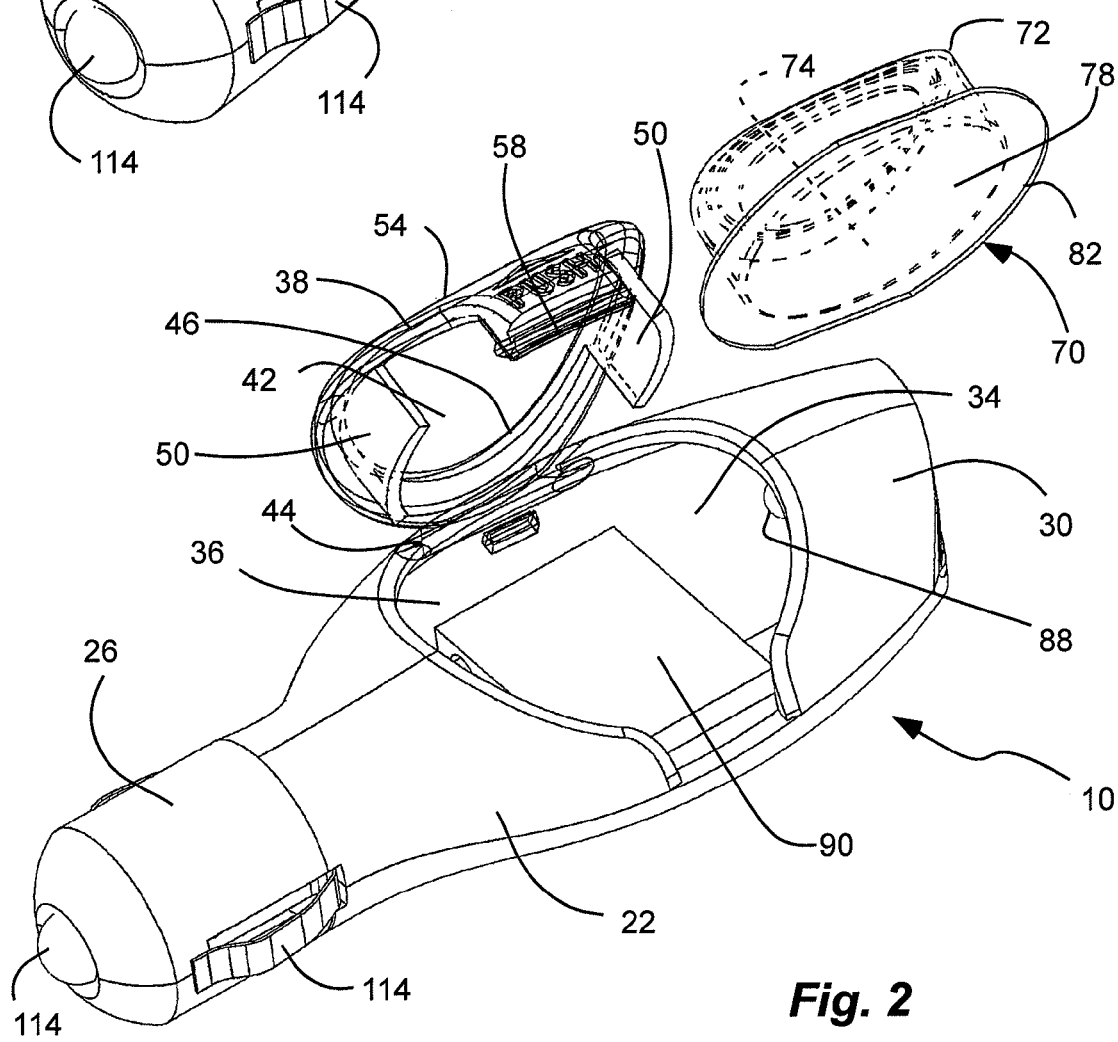
FIG. 2 is a perspective view of the air freshener of FIG. 1 with the hatch shown in an open configuration and with a scent capsule removed from a capsule cavity of the hatch.
Figure 3:
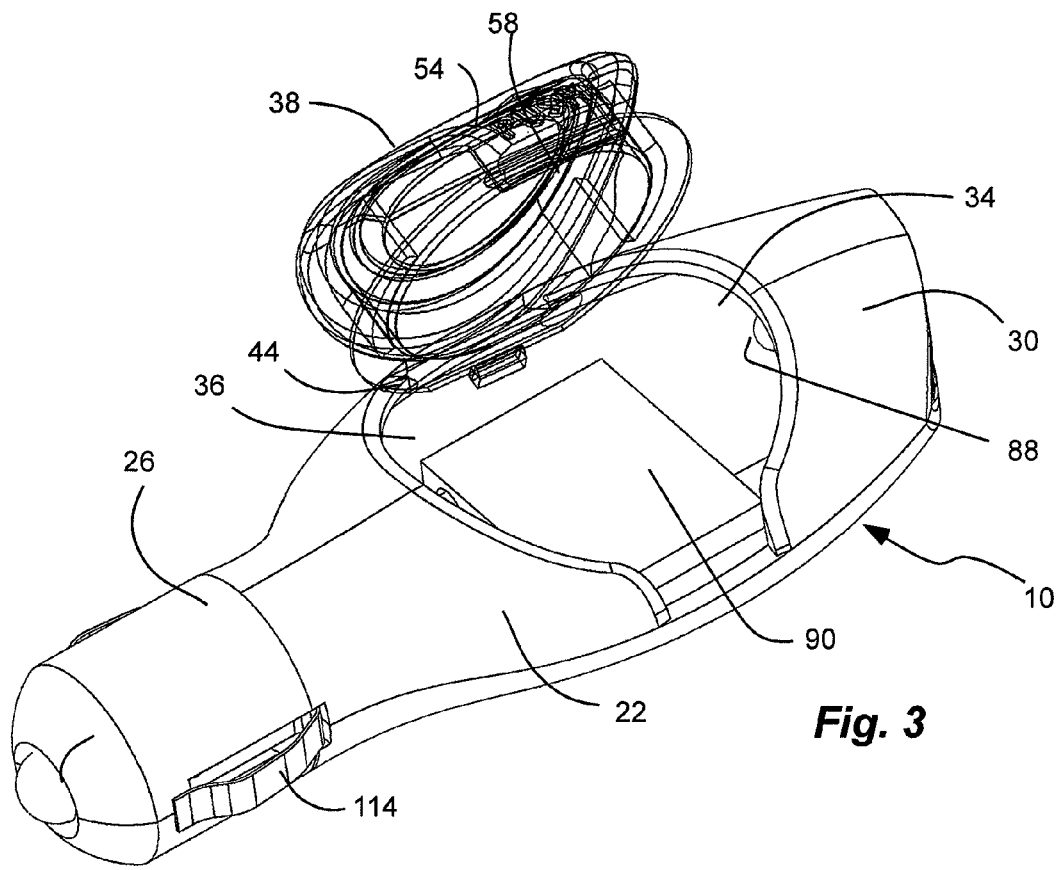
FIG. 3 is a perspective view of the air freshener of FIG. 1 with the hatch shown in an open configuration and with the scent capsule disposed in the capsule cavity of the hatch.
Figure 4:
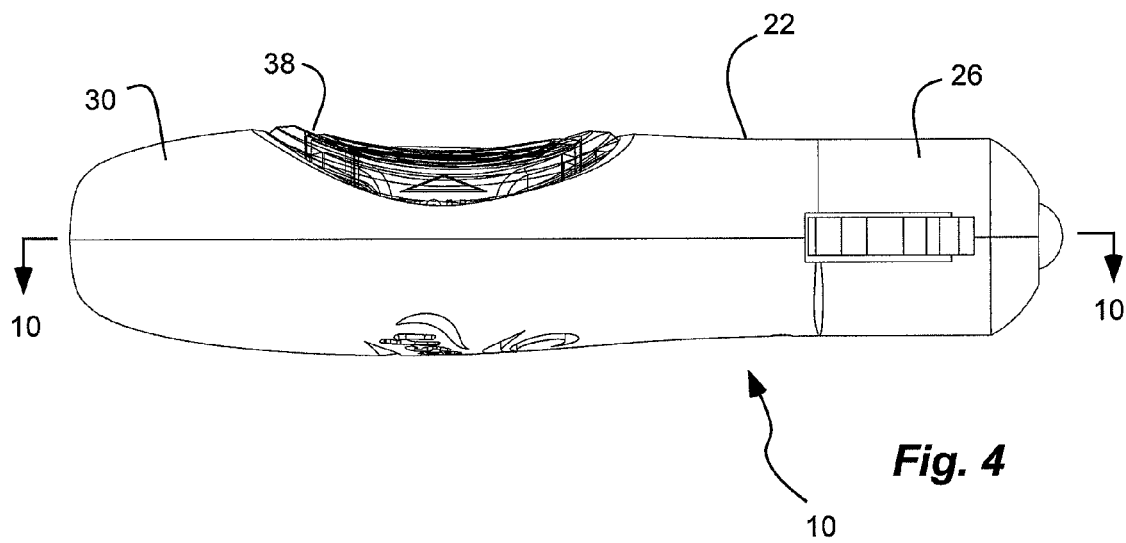
FIG. 4 is a side view of the air freshener of FIG. 1.
Figure 9:
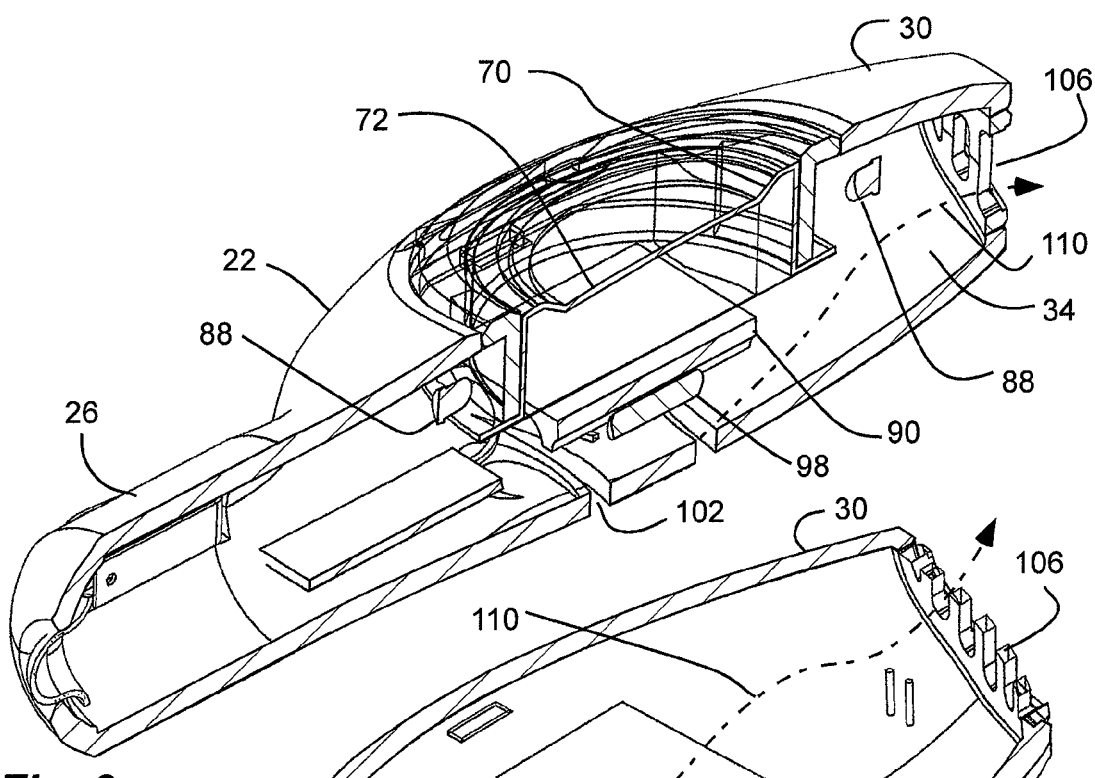
FIG. 9 is a cross-sectional perspective view of the air freshener of FIG. 1 taken along line 9 of FIG. 5.
Figure 10:
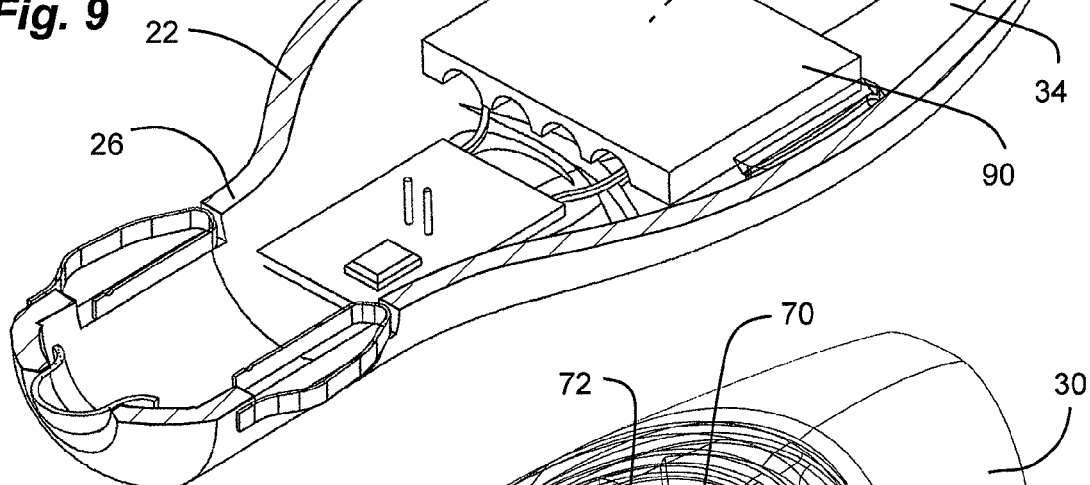
FIG. 10 is a cross-sectional perspective view of the air freshener of FIG. 1 taken along line 10 of FIG. 4.
Figure 11:
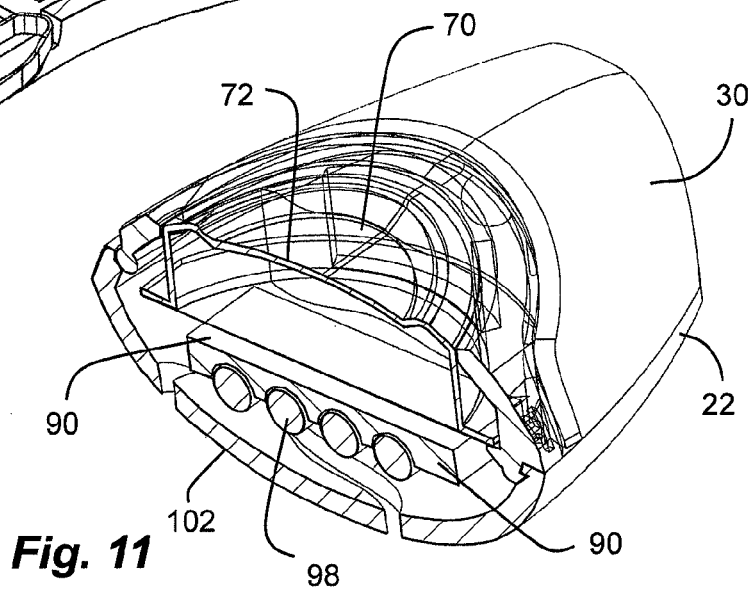
FIG. 11 is a cross-sectional perspective view of the air freshener of FIG. 1 taken along line 11 of FIG. 5.
Figure 12:
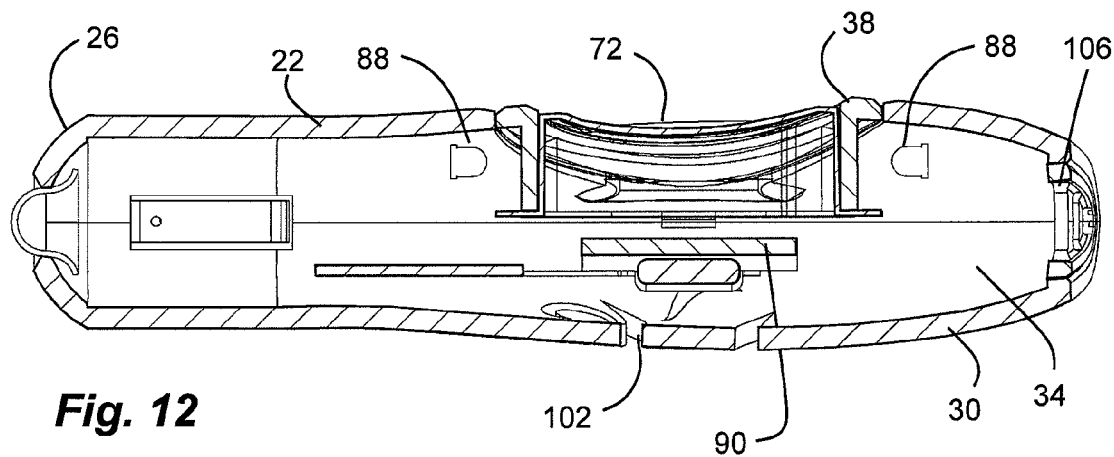
FIG. 12 is a cross-sectional perspective view of the air freshener of FIG. 1 taken along line 9 of FIG. 5.
Figure 13:
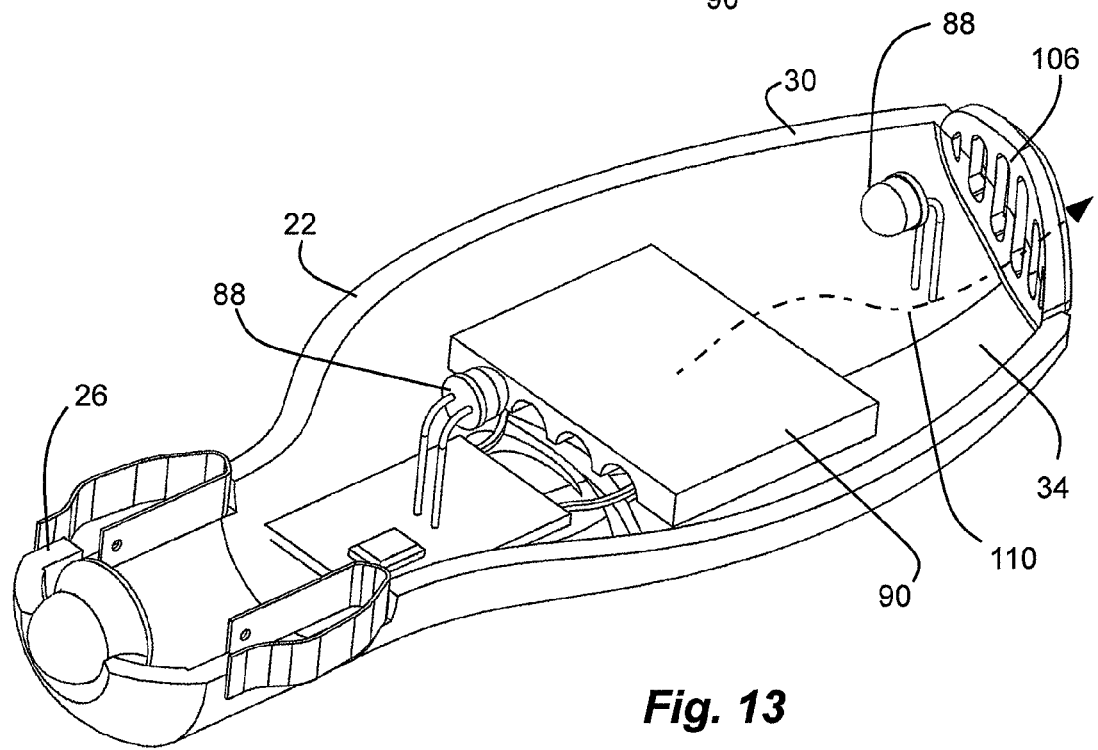
FIG. 13 is a perspective view of the air freshener of FIG. 1 with a top portion of the housing, the hatch and the scent capsule removed.
Figure 14:
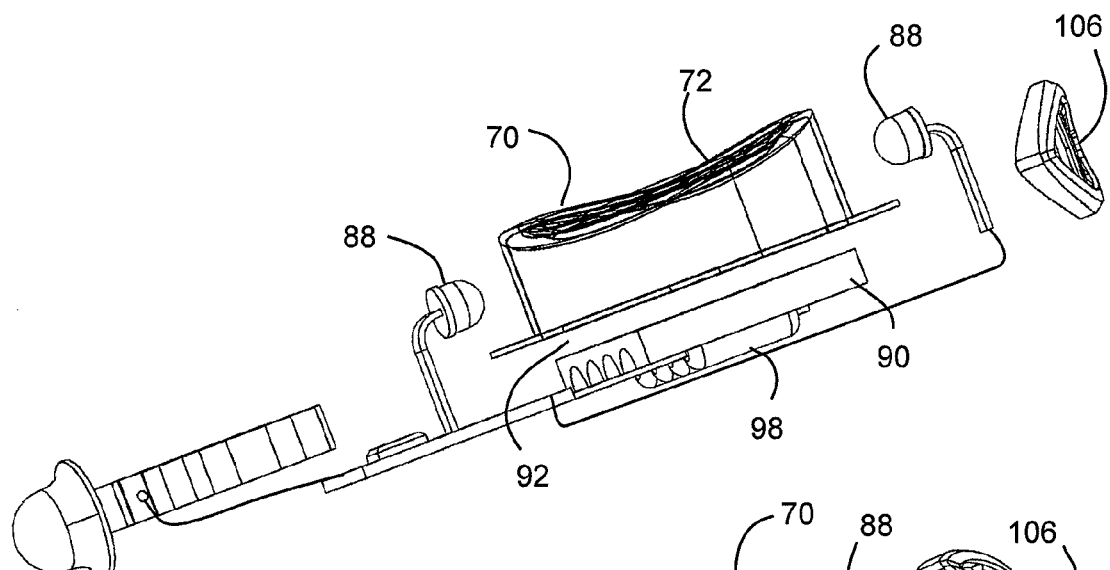
FIG. 14 is a perspective view of the air freshener of FIG. 1 with the housing and the hatch removed to show the inner components of the air freshener.
Figure 15:
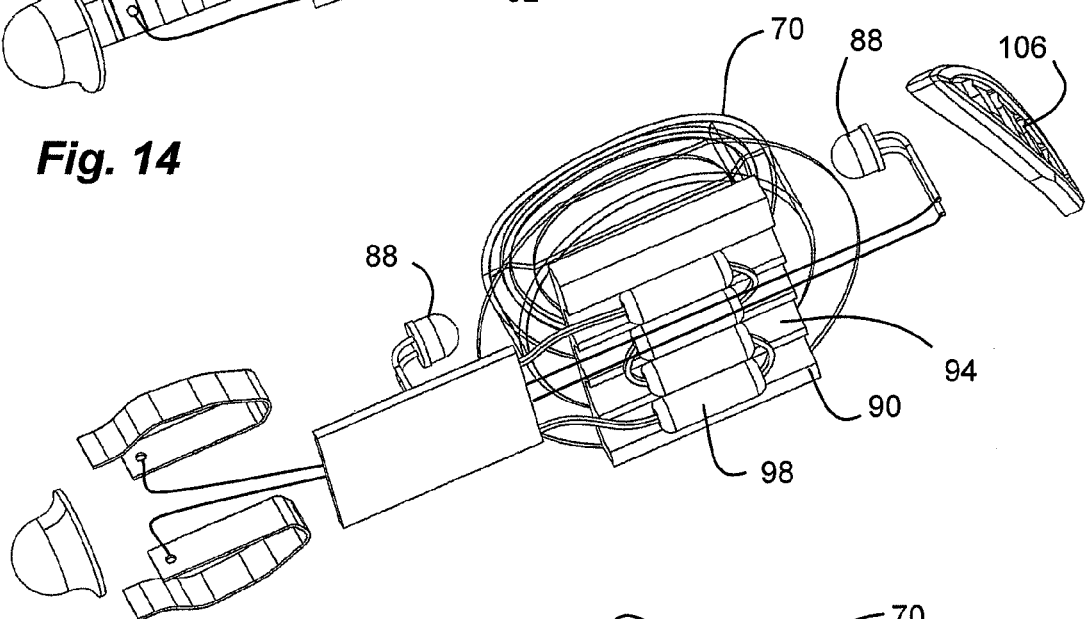
FIG. 15 is a perspective view of the air freshener of FIG. 1 with the housing and the hatch removed to show the inner components of the air freshener.
Figure 16:
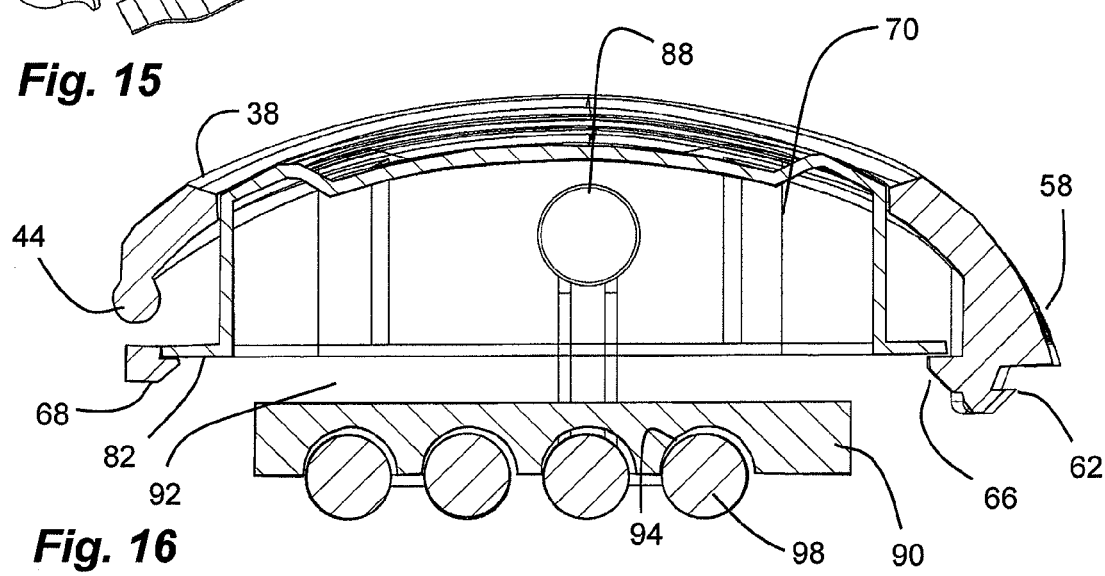
FIG. 16 is a partial cross-sectional end view of the air freshener of FIG. 1 taken along line 10 of FIG. 5 and with the housing removed.
Figure 17:
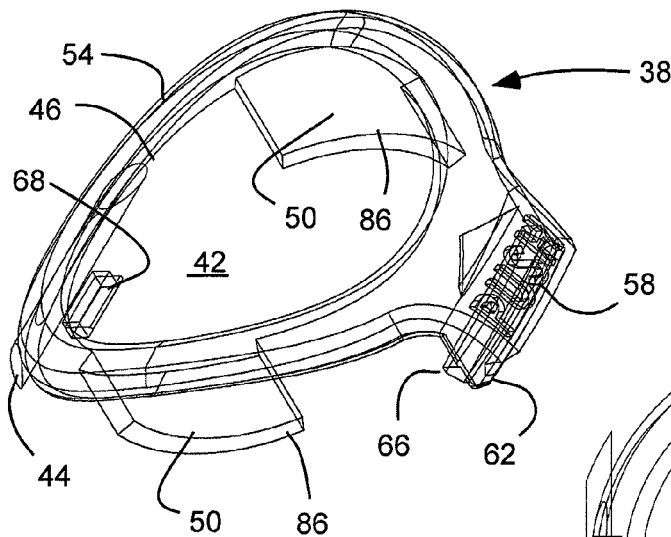
FIG. 17 is a perspective view of the hatch of the air freshener of FIG. 1.
Figure 18:
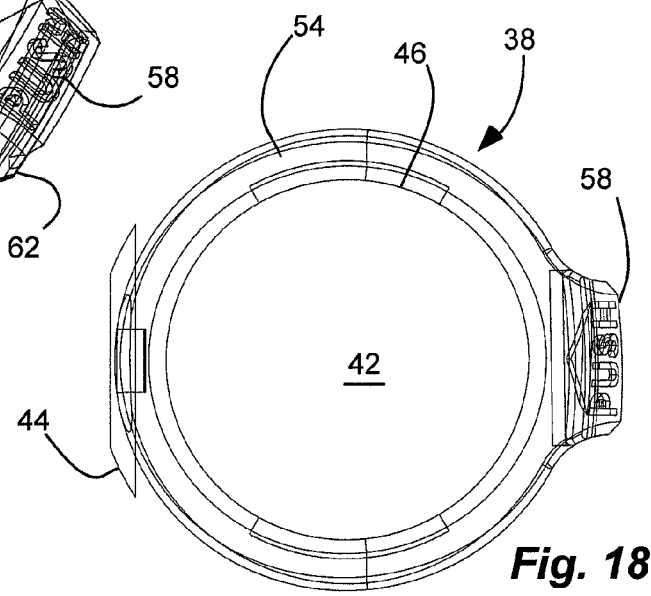
FIG. 18 is a top view of the hatch of the air freshener of FIG. 1.
Figure 19:
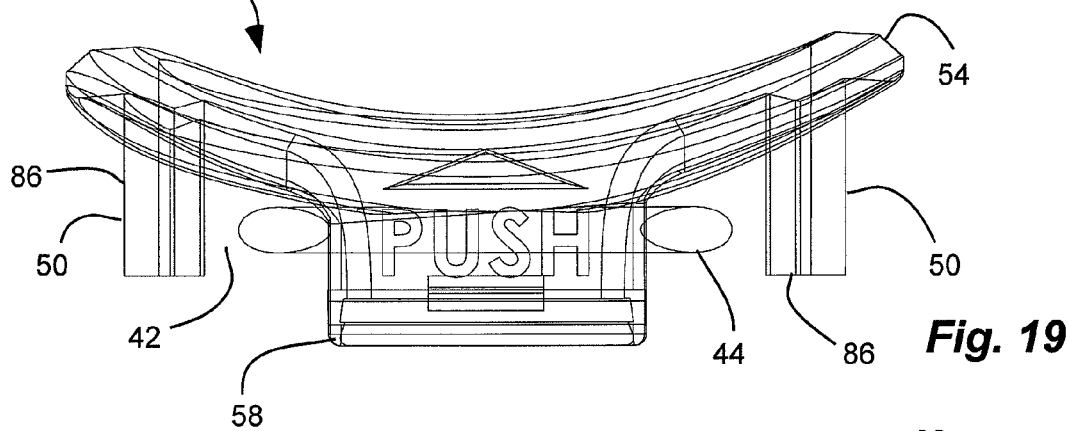
FIG. 19 is a side view of the hatch of the air freshener of FIG. 1.
Figure 20:
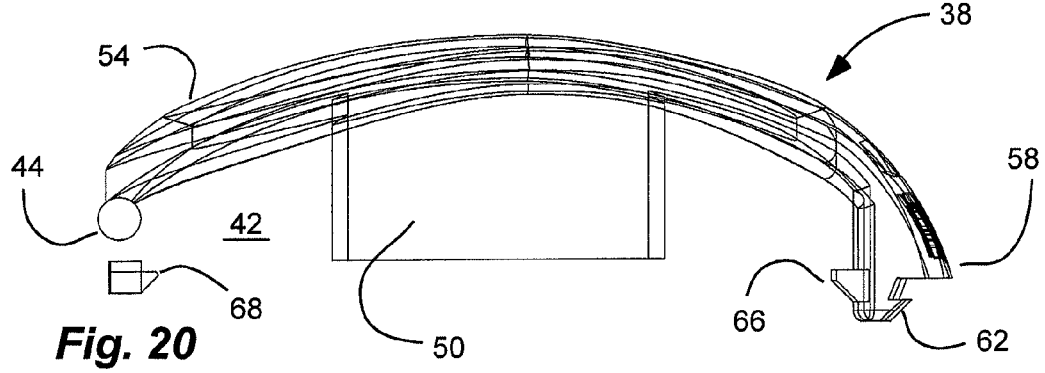
FIG. 20 is an end view of the hatch of the air freshener of FIG. 1.
Figure 21:
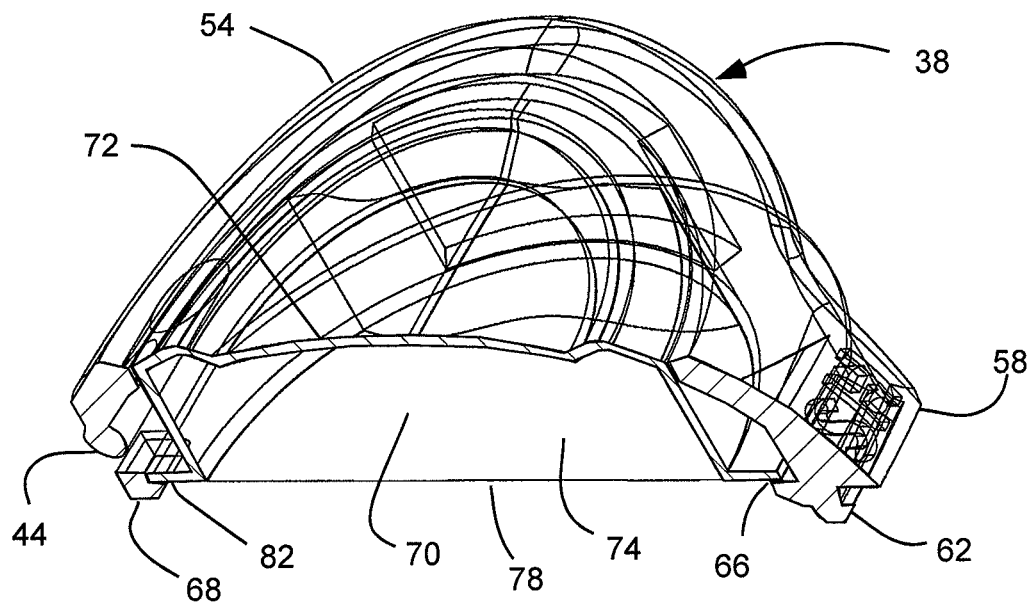
FIG. 21 is a cross-sectional end view of the hatch and scent capsule of the air freshener of FIG. 1.
Figure 22:
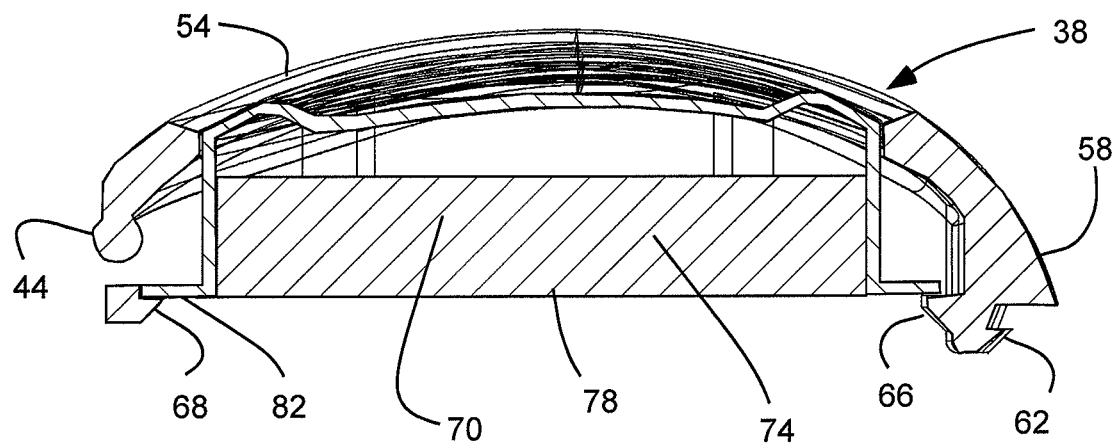
FIG. 22 is a cross-sectional end view of the hatch and the scent capsule of the air freshener of FIG. 1.
Figure 23:
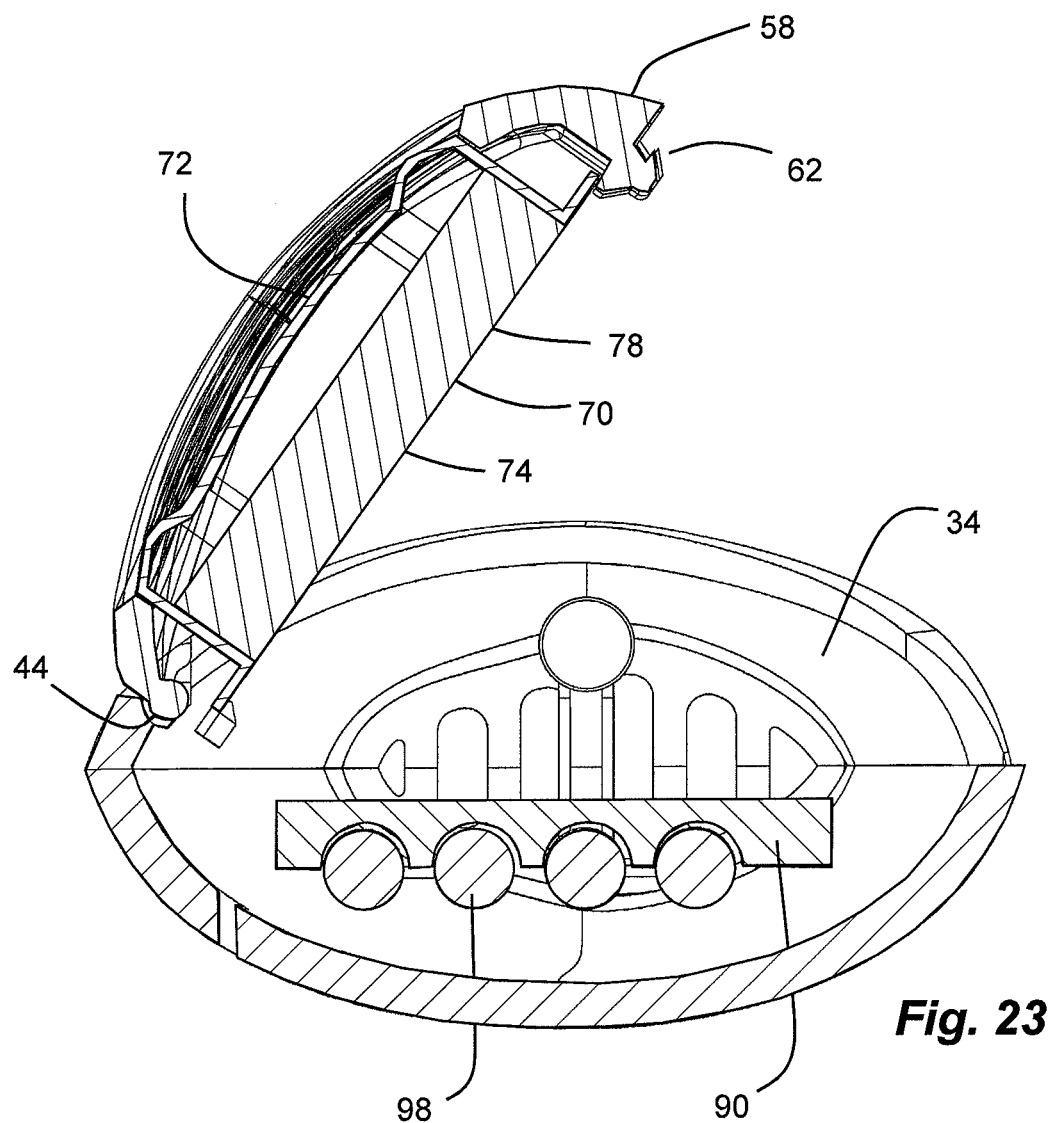
FIG. 23 is a cross-sectional end view of the air freshener of FIG. 1 taken along line 10 in FIG. 5 with the hatch in the open position.
Figure 24:
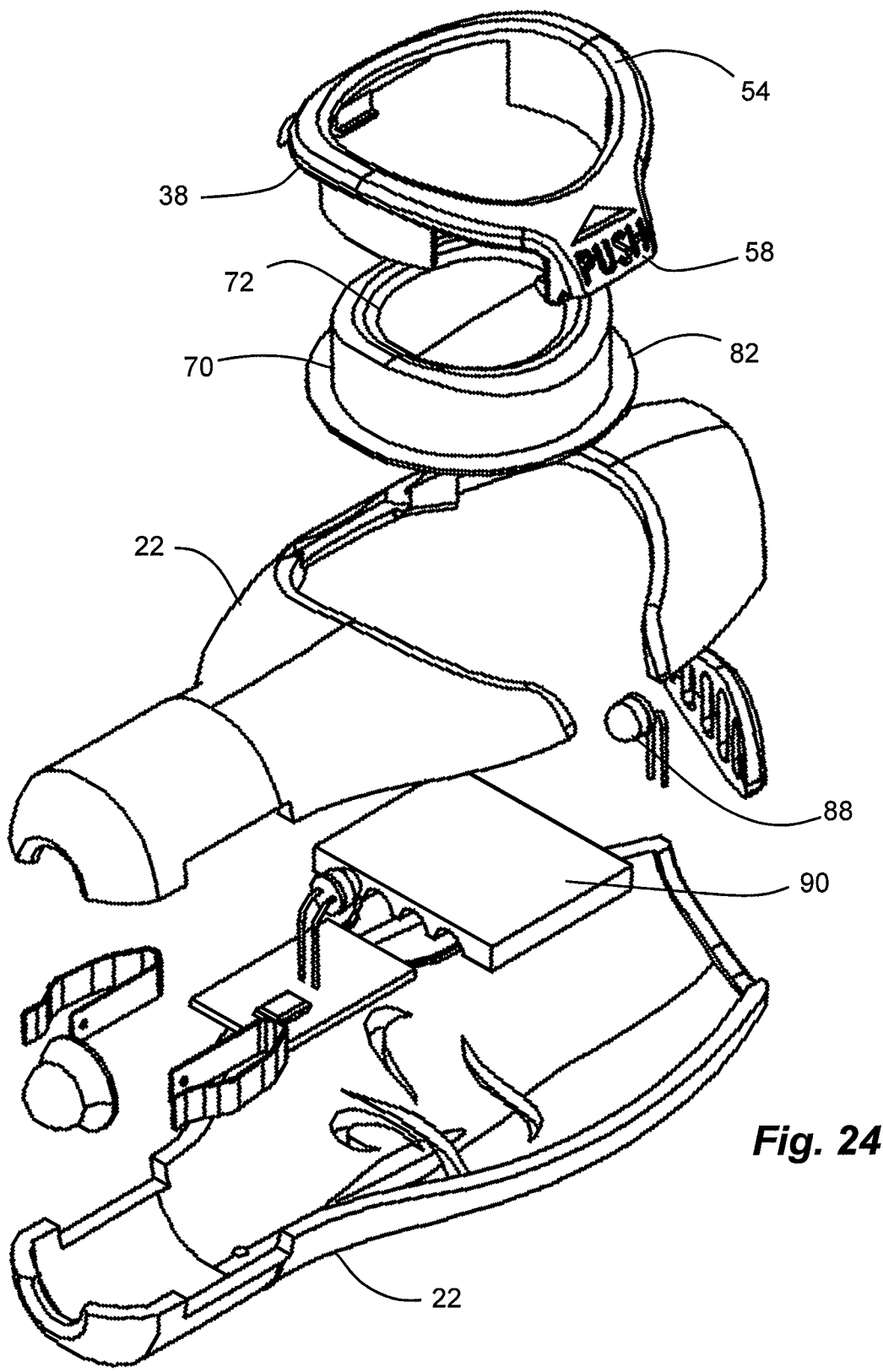
FIG. 24 is an exploded view of the air freshener of FIG. 1.
Figure 25:
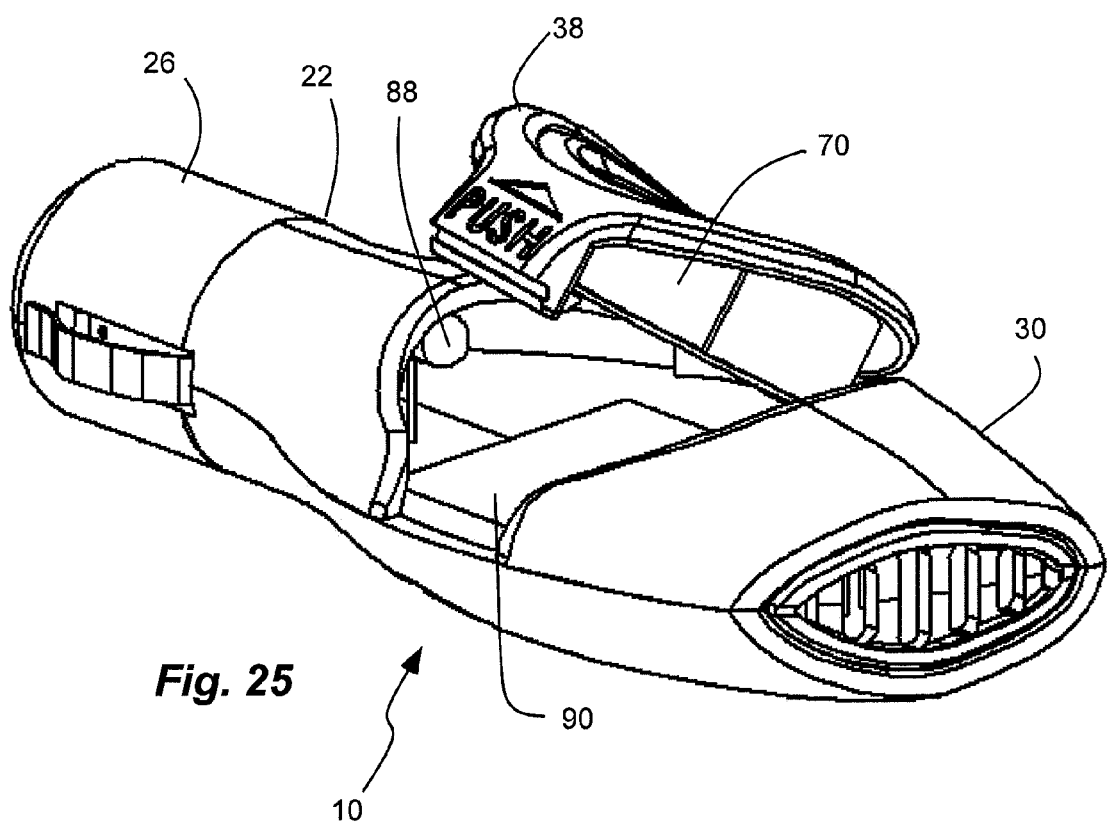
FIG. 25 is a perspective view of the air freshener of FIG. 1 shown with the hatch open.

As illustrated in FIGS. 1-25, an air freshener device, indicated generally at 10, in an example implementation in accordance with the invention is shown for use with a power outlet of an automobile or vehicle, such as a 12 volt power outlet. Such an outlet is a power outlet for an accessory or cigarette lighter, and is often located in a dash or console of a vehicle. The air freshener can use power from the vehicle to power a heat source to accelerate dispersion of a fragrance, etc. The air freshener can provide a desired and/or aesthetically pleasing scent, fragrance, aroma or neutralizing agent. Air fresheners are one example of a field that can benefit from the present invention.

The air freshener 10 includes a housing 22 with a stem 26 and a head 30 with a cavity 34 therein. The stem 26 can protrude downwardly when vertically oriented and/or with respect to a vertically oriented power outlet, and inwardly into the outlet; while the head 30 can face or protrude upward when vertically oriented and/or with respect to a vertically oriented power outlet, and outward from the outlet. It will be appreciated that downward and upward are relative to one another base on the orientation of the power outlet, which can face upward, laterally outward (substantially horizontally), or at an incline. The stem 26 can be removably coupled to the outlet so that the air freshener can be inserted as a retrofit accessory, and withdrawn as desired. The stem 26 is sized and shaped to be inserted into the power outlet, such as a 12 volt outlet, of the automobile, and includes a pair of terminals or electrical contacts thereon capable of contacting mating terminals in the power outlet. The pair of terminals can include a bottom tip terminal and one or more lateral terminals, corresponding to a bottom terminal and one or more lateral terminals in the power outlet, respectively.

The head 30 can be bulbous and/or oblong, with a diameter or lateral dimension (width and/or depth) greater than the stem 26. In addition, the head 30 and the stem 26 can be rigid and/or fixed with respect to one another. Alternatively, the head and the stem can be pivotally coupled together so that the head can pivot to a different orientation despite the orientation of the power outlet. In addition, the head and the stem can be flexible coupled together so that the head can be both pivoted and displaced with respect to the stem and the power outlet. The housing 22 can be formed by housing halves that snap or otherwise attached together, such as with adhesive or fasteners. The housing or halves thereof can be formed of plastic by injection molding. The cavity 34 of the head 30 can extend into the stem 26. A hatch cavity 36 is disposed in the housing 22, and namely in the head 30 thereof. The hatch cavity 36 can be a portion of the cavity 34 of the head.

A hatch 38 can be pivotally coupled to the housing 22 and/or the head 30, and can form a portion of the bulbous head 30. The hatch 38 can removably carry a scent capsule (70 as described in greater detail below), and removably position the scent capsule in the cavity of the housing adjacent a heat source (as described in greater detail below). The hatch 38 can span the width or shape of the head 30 so that the head and hatch and scent capsule are optimally and efficiently sized. The hatch 38 can pivot between an open and a closed position to allow removal, insertion and/or replacement of a scent capsule, as described below. In the open position, the hatch 38 can extend from the housing 22 and/or head 30, and be disposed out of the hatch cavity 36, as shown in FIGS. 2, 3, 23 and 25. Thus, the hatch 38 can be pivoted open and out of the head 30, carrying the scent capsule 70 therewith, to allow removal, and insertion or replacement, of the scent capsule. In the closed position, the hatch 38 can be disposed in the hatch cavity 36, and thus in the housing 22 and/or head 30, as shown in FIGS. 1, 4-8, 12 and 16. The hatch 38, or an exterior surface thereof, can be substantially flush with the housing 22 and/or body 30 in the closed position. In the closed position, the hatch 38 is substantially contained within the hatch cavity 36, and has an outer surface that is substantially flush with an exterior of the housing 22. The hatch 38 can be pivoted closed and into the head 30, carrying the scent capsule 70 therewith, to insert the scent capsule 70 into the head 30 or cavity 34 thereof. The hatch 38 can have a capsule cavity 42 therein that faces an interior or cavity 34 of the housing 22 or head 30 in the closed position. The capsule cavity 42, and thus the hatch 38, can receive and carry a scent capsule 70, as discussed in greater detail below. A hinge can be disposed between or formed between the hatch 38 and the housing 22 about which the hatch pivots between open and closed positions. The hatch 38 can include a hinge member 44 formed integrally therewith, such as an axle, that is received in another hinge member formed in the housing. The hatch can be formed of plastic by injection molding. The hatch or at least a portion thereof can be transparent or at least translucent.

The hatch 38 can have an exterior window 46 in the outer surface of the hatch, and an interior window 50 in the hatch facing an interior of the cavity 34 in the closed position. In one aspect, the exterior window 46 of the hatch 38 can include an aperture. The hatch 38 can include or can be formed by an annulus 54 disposable in the hatch cavity 36 of the housing 22. The annulus 54 can have an aperture 46 therein forming the exterior window. The hinge can include a hinge member 44 disposed on a lateral side of the annulus 54. A finger 58 can be carried by the hatch 38 and/or annulus 54 opposite the hinge or hinge member 44. The finger 58 can be displaceable or bendable to unlock the hatch 28. Thus, the finger 58 can be a finger latch disposed on another lateral side of the annulus 54 opposite the hinge member 44. The finger 58 can include a lock flange 62 on a distal free end of the finger to releasably engage the housing 22, or flange thereof. Displacing or bending the finger 58 disengages the lock flange 62 of the finger 58 from the flange of the housing. The finger 58 can also include a retention flange 66 on the distal free end of the finger, opposite the lock flange 62, to releasably engage the scent capsule 70 as discussed below. The hatch 38 and/or annulus 54 can have opposite flanges 66 and 68 on opposite sides of the hatch or annuls to retain the scent capsule 70. In addition, the hatch 38 can include one or more lateral windows 50, on the perimeter sides thereof. In another aspect, the exterior window 46 can be formed by a transparent or translucent portion. The hatch or annulus can be formed of plastic by injection molding. The hatch or annulus or at least a portion thereof can be transparent or at least translucent.

As indicated above, a scent capsule 70 can be removably carried by the hatch 38 and/or annulus 54, and thus the head 30 of the housing 22. The scent capsule 70 can be disposed in the capsule cavity 42 of the hatch 38 and/or annulus 54, and thus the cavity 34 of the housing 22. Thus, the scent capsule 70 can pivot or displace with the hatch 38. The scent capsule 70 can have a chamber 72 containing a fragrant and/or scented material or liquid 74, and can have a substantially flat permeable membrane 78 through which a fragrance of the fragrant material can permeate over time. The chamber 72 can form a vessel covered or sealed by the membrane 78. Thus, together, the chamber and the membrane form a container for the fragrant material. The chamber 72 can be or can include a clear dome through which light can pass and the fragrant material can be viewed. The fragrant material can be a liquid, such as a fragrant oil. A scented liquid, such as oil, can be colored so that it translucent to aid in visibility. The liquid or oil can also move in the chamber or vessel to aid in visibility. The permeable membrane 78 can be located adjacent a heat element or heat plate 90, as discussed in greater detail below. The membrane 78 can be in close proximity to, and directly in front of, the heat plate 90, separated therefrom by a gap 92. Thus, the membrane 78 and the heat plate 90 can be separated from one another and in a non-contacting relationship. The permeable membrane 78 and the surface of the heat plate 90 can be substantially flat. The membrane 78 can face towards the heat plate 90 so that heat therefrom is directed against the membrane. The scent capsule 70 can include at least opposite flanges on opposite sides of the chamber 72 of the scent capsule. For example, an annular perimeter flange 82 can circumscribe the chamber 72 of the scent capsule 70. The opposite flanges and/or the annular perimeter flange 82 can be engaged by the opposite flanges 66 and 68 of the hatch 38 and/or annulus 54 to retain the scent capsule 70 therein.

As described above, opposite flanges 66 and 68 on opposite sides of the hatch 38 and/or annulus 54 can engage and retain the opposite flanges of the scent capsule 70 in the capsule cavity 42 of the hatch 38 and/or annulus 54. A slot can be formed in the capsule cavity, such as by the flanges of the hatch, to removably receive the flange(s) 82 of the scent capsule. The hatch 38 and/or annulus 54 can also include a pair of arms 86 disposed on the annulus on opposite sides of the aperture 46 and extending into the cavity to abut to the flange(s) 82 of the scent capsule 70. The arms 86 provide an opposing force to the flanges 66 and 68 on the perimeter flange 82 of the scent capsule 70 to maintain the position of the scent capsule. Thus, the flange(s) 82 of the scent capsule 70 is held between the arms 86 and the flanges 66 and 68 of the hatch or annulus. The arms 86 can be transparent or translucent to form the lateral window(s) 50.

The scent capsule 70 or chamber 72 thereof can include or can form a dome that can be transparent or at least translucent such that the scent material 74 therein can be visible. The dome of the sent capsule 70 can extend at least to the window 46 or aperture of the hatch 38 or annulus 54. The clear dome of the scent capsule 70 can project into the aperture, without extending through the aperture, or out of the hatch 38 or head 30. Thus, the hatch 38 or annulus 54, or a portion thereof surrounding the aperture, can protect the clear dome. In one aspect the dome can extend into the aperture, and can be flush with an exterior of the hatch 38 and the housing 22. A light source, such as one or more light emitting diodes (LEDs) 88 can be disposed adjacent to the lateral window(s) 50 to illuminate the scent material 74 and increase visibility through the window 46. Light from the light source can pass through the lateral window 50 or arms 86 of the annulus 54 or hatch 38, through the chamber 72 or dome thereof, through or around the scent material 74, through the chamber or dome, and through the window 46 or aperture of the hatch 38 or annulus 54. The light source or LEDs 88 can be coupled to the electrical coupling or terminals of the housing, and thus the power outlet. Thus, the amount of scent material remaining can be ascertained. The housing and the hatch or annulus can be opaque. Indicia can be disposed on the chamber or dome of the scent capsule, and visible through the window 46 of the hatch or annulus.

A heat source such as a heat plate 90 can be disposed in the housing 22 adjacent the hatch cavity 36 and opposing the permeable membrane 78 of the scent capsule 70 when the hatch 38 is in the closed position. A gap 92 can be formed between the heat plate 90 and the permeable membrane 78 of the scent capsule 70 to create an air flow path. The heat from the heat plate 90 can heat the fragrant material 74 in the scent capsule 70, and accelerate permeation of the fragrant material through the permeable membrane 78 of the scent capsule 70. The heat plate can be formed of a solid block of material, including metal, such as aluminum. The heat plate can have a flat surface facing a flat surface of the permeable membrane to create the gap. The heat plate 90 can have a plurality of grooves 94 therein to receive a plurality of resistors 98 disposed in the grooves. The grooves can be formed in an opposite side of the heat plate opposite the scent capsule. Thus, the heat plate forms a barrier between the resistors or heating elements and the membrane to protect the membrane from overheating and melting. The grooves 94 form fins therebetween to increase the surface area available to gather heat from the resistors 98. The resistors 98 can be electrically coupled to the electrical coupling or terminals of the housing, and thus the power outlet.

The head 30 of the housing 22 can have an inlet vent aperture(s) 102, and an outlet vent aperture(s) 106. The inlet vent aperture 102 can be adjacent the heat plate 90. An air flow path 110 can be defined through head 30 of the housing 22, in through the inlet vent aperture 102, past the permeable membrane 78 of the scent capsule 70 and heat plate 90 (or the gap 92 therebetween), and out of the outlet vent aperture 106.

The stem 26 of the housing can carry an electrical connection 114 that can couple to the electrical outlet. The light source and the heat source can be electrically coupled to the electrical connection. Control electronics, such as a PCB board, can be carried by the housing and electrically coupled between the electrical connection and the light source and the heat source. The heat source or the control electronics can include a timer and/or a temperature sensor to limit the heat of the heat source or heat plate.

In another aspect, the air freshener device can also include an air displacement mechanism, such as a powered fan, such as a motor powered fan. An air displacement mechanism is carried by the housing and/or head, and disposed in the cavity. The air displacement mechanism can include a rotatable fan or turbine, a motor coupled to the fan to rotate the fan, and the motor coupled to the pair of terminals to power the motor. The fan can be an axial-flow fan with blades, such as propeller style blades, that force air to move parallel to the shaft about which the blades rotate. Alternatively, the fan can be a centrifugal fan with an impeller carrying blades and blowing air at a right angle to the intake of the fan. Alternatively, the fan can be a cross-flow or tangential fan. The housing can include a motor mount or brace between the fan and motor and coupled to the housing. The motor or a portion thereof can nest in the stem with an opposite end or shaft held by the motor mount or brace. The air displacement mechanism can further include a manual switch electrically coupled between the motor and the pair of terminals to selectively activate and deactivate the air displacement mechanism. The switch can be any type of switch, including a slide type switch, a push button type switch, etc. A timer circuit can be coupled to the switch to deactivate the fan or the turbine after a predetermined amount of time. Alternatively, the housing, or stem, can be inserted and withdrawn from the power outlet to activate and deactive the air freshener. The air freshener can include control electronics on a printed circuit board disposed in the housing and electrically coupled to the pair of contacts, the motor, the switch and/or the lights, etc.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:

1. An air freshener device configured to be carried by a cigarette lighter style power outlet of an automobile having a bottom terminal and at least one lateral terminal, the device comprising:
    a) a housing with a stem and a head with a cavity therein, the stem sized and shaped to be inserted into the cigarette lighter style power outlet of the automobile, and the stem having a bottom tip terminal and at least one lateral terminal corresponding to the bottom terminal and the at least one lateral terminal of the cigarette lighter style power outlet;
    b) a scent capsule disposed in the housing and having a chamber containing a fragrant material and having a permeable membrane through which a fragrance of the fragrant material can permeate over time; and
    c) a heat source disposed in the housing adjacent and opposing the permeable membrane of the scent capsule capable of being powered by the power outlet of the automobile to heat the fragrant material in the scent capsule and accelerate permeation of the fragrant material through the permeable membrane of the sent capsule.

2. A device in accordance with claim 1, further comprising: a heat plate; and
a gap between the heating plate and the permeable membrane of the scent capsule.

3. A device in accordance with claim 2, further comprising: a plurality of grooves in the heat plate; and
a plurality of resistors disposed in the grooves.

4. A device in accordance with claim 1, further comprising:
    a) a hatch cavity in the head of the housing;
    b) a hatch pivotally coupled to the housing and substantially contained within the hatch cavity with an outer surface that is substantially flush with an exterior of the housing in a closed position, and with a capsule cavity therein facing an interior of the housing in the closed position; and
    c) the scent capsule removably disposed in the capsule cavity of the hatch and carried by the hatch as the hatch pivots, the permeable membrane facing the interior of the cavity in the closed position.

5. A device in accordance with claim 4, further comprising:
    a) the chamber of the scent capsule being at least light translucent;
    b) an exterior window in the outer surface of the hatch;
    c) an interior window in the hatch facing an interior of the cavity in the closed position; and d) a light disposed in the housing adjacent the interior window of the hatch when the hatch is in the closed position configured to illuminate the scent material in the scent capsule so that the scent material is visible through the exterior window of the hatch.

6. A device in accordance with claim 4, further comprising:
an exterior window in the outer surface of the hatch;
an aperture in the exterior window; and
the chamber of the scent capsule including a dome portion extending at least to the aperture.

7. A device in accordance with claim 4, further comprising:
a) opposite flanges on opposite sides of the chamber of the scent capsule; and
b) opposite flanges on opposite sides of the hatch engaging and retaining the opposite flanges of the scent capsule in the capsule cavity of the hatch.

8. A device in accordance with claim 4, further comprising:
a) a hinge between the hatch and the housing about which the hatch pivots between open and closed positions;
b) a finger carried by the hatch opposite the hinge and being displaceable to unlock the hatch;
c) a lock flange on a distal free end of the finger and releasably engaging the housing; and
d) a retention flange on the distal free end of the finger opposite the lock flange to releasably engage the scent capsule.

9. A device in accordance with claim 1, wherein the stem is circular.

10. A device in accordance with claim 1, wherein the head is bulbous; and further comprising:
a) a hatch coupled to the housing and displaceable with respect to the housing; and
b) the hatch forming part of the bulbous head.

11. A device in accordance with claim 1, further comprising:
a) a hatch coupled to the housing and displaceable with respect to the housing, the hatch having a capsule cavity therein facing an interior of the housing; and
b) the scent capsule removably disposed in the capsule cavity of the hatch.

12. A device in accordance with claim 1, further comprising:
a) a hatch coupled to the housing and displaceable with respect to the housing,
b) an exterior window in an outer surface of the hatch; and
c) the scent capsule having a dome that is at least translucent so that the fragrant material is visible through the dome and the exterior window of the hatch.

13. An air freshener device configured to be carried by a power outlet of an automobile, the device comprising:
a) a housing with a stem and a head with a cavity therein, the stem sized and shaped to be inserted into the power outlet of the automobile;
b) a hatch cavity in the head of the housing;
c) a hatch pivotally coupled to the housing and substantially contained within the hatch cavity with an outer surface that is substantially flush with an exterior of the housing in a closed position, and with a capsule cavity therein facing an interior of the housing in the closed position; and
d) a scent capsule removably disposed in the capsule cavity of the hatch and carried by the hatch as the hatch pivots, the scent capsule having a chamber containing a fragrant material and having a permeable membrane through which a fragrance of the fragrant material can permeate over time, the permeable membrane facing the interior of the cavity in the closed position.

14. A device in accordance with claim 13, further comprising:
a) the chamber of the scent capsule being at least light translucent;
b) an exterior window in the outer surface of the hatch;
c) an interior window in the hatch facing an interior of the cavity in the closed position; and
d) a light disposed in the housing adjacent the interior window of the hatch when the hatch is in the closed position configured to illuminate the scent material in the scent capsule so that the scent material is visible through the exterior window of the hatch.

15. A device in accordance with claim 13, wherein the exterior window of the hatch includes an aperture; and wherein the chamber of the scent capsule includes a dome portion extending at least to the aperture.

16. A device in accordance with claim 13, further comprising:
a) opposite flanges on opposite sides of the chamber of the scent capsule; and
b) opposite flanges on opposite sides of the hatch engaging and retaining the opposite flanges of the scent capsule in the capsule cavity of the hatch.

17. A device in accordance with claim 13, further comprising:
a) a hinge between the hatch and the housing about which the hatch pivots between open and closed positions;
b) a finger carried by the hatch opposite the hinge and being displaceable to unlock the hatch;
c) a lock flange on a distal free end of the finger and releasably engaging the housing; and
d) a retention flange on the distal free end of the finger opposite the lock flange to releasably engage the scent capsule.

18. A device in accordance with claim 13, further comprising:
a heat source disposed in the housing adjacent and opposing the permeable membrane of the scent capsule capable of being powered by the power outlet of the automobile to heat the fragrant material in the scent capsule and accelerate permeation of the fragrant material through the permeable membrane of the sent capsule.

19. A device in accordance with claim 18, further comprising:
a heat plate; and
a gap between the heating plate and the permeable membrane of the scent capsule.

20. A device in accordance with claim 19, further comprising:
a plurality of grooves in the heat plate; and
a plurality of resistors disposed in the grooves.

21. An air freshener device configured to be carried by a power outlet of an automobile, the device comprising:
a) a housing with a stem and a head with a cavity therein, the stem sized and shaped to be inserted into the power outlet of the automobile;
b) a hatch cavity in the head of the housing;
c) a hatch pivotally coupled to the housing and substantially contained within the hatch cavity with an outer surface that is substantially flush with an exterior of the housing in a closed position, and with a capsule cavity therein facing an interior of the housing in the closed position;
d) an exterior window in the outer surface of the hatch;
e) an interior window in the hatch facing an interior of the cavity in the closed position;

f) a scent capsule removably disposed in the capsule cavity of the hatch and carried by the hatch as the hatch pivots, the scent capsule having a chamber containing a fragrant material and having a permeable membrane through which a fragrance of the fragrant material can permeate over time, the permeable membrane facing the interior of the cavity in the closed position, the chamber being at least light translucent;

g) a heat plate disposed in the housing adjacent the hatch cavity and opposing the permeable membrane of the scent capsule when the hatch is in the closed position configured to heat the fragrant material in the scent capsule and accelerate permeation of the fragrant material through the permeable membrane of the sent capsule;

h) a light disposed in the housing adjacent the interior window of the hatch when the hatch is in the closed position configured to illuminate the scent material in the scent capsule so that the scent material is visible through the exterior window of the hatch; and i) an inlet vent in the housing adjacent the heat plate, an outlet vent in the housing configured to allow release of the fragrant material from the housing, and an air flow path defined therebetween.

22. A device in accordance with claim 21, wherein the hatch spans a width of the head of the housing.

23. A device in accordance with claim 21, wherein the exterior window of the hatch includes an aperture; and wherein the chamber of the scent capsule includes a dome portion extending at least to the aperture.

24. A device in accordance with claim 21, further comprising:
   a gap between the heating plate and the permeable membrane of the scent capsule.

25. A device in accordance with claim 24, further comprising:
   a plurality of grooves in the heat plate; and
   a plurality of resistors disposed in the grooves.

* * * * *